(12) United States Patent
Falkenberg

(10) Patent No.: US 11,235,118 B2
(45) Date of Patent: Feb. 1, 2022

(54) TRACHEOSTOMA DEVICE HOLDER

(71) Applicant: Atos Medical AB, Horby (SE)

(72) Inventor: Richard Falkenberg, Horby (SE)

(73) Assignee: ATOS MEDICAL AB ( * ) Notice: Subject to any disclaimer, the term of this patent is extended or adjusted under 35 U.S.C. 154(b) by 427 days.

(21) Appl. No.: 16/075,647

(22) PCT Filed: Jan. 24, 2017

(86) PCT No.: PCT/SE2017/050064
§ 371 (c)(1),
(2) Date: Aug. 4, 2018

(87) PCT Pub. No.: WO2017/135867
PCT Pub. Date: Aug. 10, 2017

(65) Prior Publication Data
US 2020/0139063 A1 May 7, 2020

(30) Foreign Application Priority Data
Feb. 4, 2016 (SE) .................... 1650136-3

(51) Int. Cl.
A61M 16/04 (2006.01)
A61M 25/02 (2006.01)

(52) U.S. Cl.
CPC ... *A61M 16/047* (2013.01); *A61M 2025/0266* (2013.01); *A61M 2207/10* (2013.01)

(58) Field of Classification Search
CPC ............ A61M 16/047; A61M 16/0465; A61M 16/0466; A61M 16/0467; A61M 16/0468;
(Continued)

(56) References Cited

U.S. PATENT DOCUMENTS 3,920,009 A * 11/1975 Olsen .................. A61M 16/047
128/201.13
4,775,374 A * 10/1988 Cilento ............. B29C 66/24221
604/344

(Continued)

FOREIGN PATENT DOCUMENTS

EP 0078685 A1 5/1983
EP 1254647 A1 11/2002
(Continued)

OTHER PUBLICATIONS

N. Baït, B. Grassl, C. Derail, A. Benaboura, Hydrogel nanocomposites as pressure-sensitive adhesives for skin-contact applications Soft Matter (2011), 7 , p. 2025. (Year: 2011).*

(Continued)

*Primary Examiner* — Rachel T Sippel
*Assistant Examiner* — Kelsey E Baller
(74) *Attorney, Agent, or Firm* — Fishman Stewart PLLC

(57) ABSTRACT

A tracheostoma device holder for holding a tracheostoma device superimposed of a tracheostoma of a person is provided. The tracheostoma device holder includes a flexible skirt for attachment over a tracheostoma via a skin adhesive proximal side thereof, and the skirt is provided with a through hole. A tubular tracheostoma device fitting is arranged circumferentially of the through hole, and the tubular tracheostoma device fitting extends distally from the distal side of the skirt. The skirt has at least two sheets, in form of a distal end sheet comprising a skin adhesive hydrogel or hydrocolloid, and a support sheet proximally of the distal end sheet. The support sheet includes polyurethane.

17 Claims, 4 Drawing Sheets

(58) Field of Classification Search
CPC .......... A61M 16/0472; A61M 16/0497; A61M 2025/0266; A61M 2207/10; A61F 13/128; A61F 13/02
USPC ........................................ 128/207.14, 207.29
See application file for complete search history.

(56) References Cited

U.S. PATENT DOCUMENTS

| | | | | |
|---|---|---|---|---|
| 4,778,446 | A * | 10/1988 | Jensen | A61M 1/0088 604/27 |
| 5,000,741 | A * | 3/1991 | Kalt | A61F 13/023 128/200.26 |
| 5,100,393 | A * | 3/1992 | Johnson | A61M 25/02 128/DIG. 26 |
| 5,306,504 | A * | 4/1994 | Lorenz | A61L 24/043 424/449 |
| 5,800,685 | A * | 9/1998 | Perrault | A01N 25/10 204/291 |
| 5,848,590 | A * | 12/1998 | Smith | A61M 16/0468 128/201.13 |
| 2003/0171737 | A1 * | 9/2003 | Leise, Jr. | A61F 5/448 604/540 |
| 2003/0204174 | A1 | 10/2003 | Cisko | |
| 2010/0042073 | A1 * | 2/2010 | Oster | A61M 39/0208 604/539 |
| 2010/0331785 | A1 * | 12/2010 | Fabo | A61F 13/0203 604/180 |
| 2011/0184327 | A1 * | 7/2011 | Cameron | A61F 13/12 602/43 |
| 2013/0131621 | A1 * | 5/2013 | Van Holten | A61L 15/44 604/368 |
| 2013/0192603 | A1 | 8/2013 | Leibitzki et al. | |
| 2013/0192604 | A1 | 8/2013 | Persson et al. | |
| 2013/0213404 | A1 | 8/2013 | Leibitzki et al. | |
| 2014/0194824 | A1 | 7/2014 | Schutz et al. | |

FOREIGN PATENT DOCUMENTS

| | | |
|---|---|---|
| WO | WO-9419045 A1 | 9/1994 |
| WO | 2009075636 A1 | 6/2009 |
| WO | WO-2014090549 A1 | 6/2014 |

OTHER PUBLICATIONS

Extended European Search Report dated Jun. 4, 2019 related to corresponding European Patent Application No. 11747868.2.
English translation of Chinese Office Action for CN-201780009848.2, dated Jul. 23, 2020.

* cited by examiner

TRACHEOSTOMA DEVICE HOLDER

CROSS REFERENCE TO RELATED APPLICATIONS

This application claims priority to International Application PCT/SE2017/050064 filed on Jan. 24, 2017 and Swedish Application SE 1650136-3 filed on Feb. 4, 2016, the contents of each of which are hereby incorporated by reference in their entirety.

FIELD OF THE INVENTION

This invention pertains in general to a tracheostoma aid device holder. More particularly, the present invention pertains to a tracheostoma aid device holder, comprising a skirt for attachment over a tracheostoma via the proximal side of the skirt, said skirt being provided with a through hole having a tubular tracheostoma device fitting extending distally from the skirt circumferentially of said through hole.

BACKGROUND OF THE INVENTION

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a person has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the person to speak. It is desirable that the flow of the exhaled air be controlled by means of a tracheostoma valve. In these situations, the valve can be arranged to remain open during breathing but can be closed to divert the airflow, through a small additional increase in exhaled air flow.

In this respect tracheostoma aid devices, such as filter devices, HME, breathing protectors, and speech valves, have been developed to enable moisturizing of inhaled air, removal of small particles and bacteriological substances in said inhaled air, and providing the person with the ability to speech by closing the air passage through the tracheostoma by manual operation.

These tracheostoma aid devices are held in place by a tracheostoma device holder, arranged above the tracheostoma of the person. The tracheostoma device holder is normally attached to the skin of the person by a plaster, having an adhesive surface on the side of the plaster intended to be directed towards the person in use. Either, the tracheostoma device holder is welded to the plaster, or the tracheostoma device holder is arranged on an adhesive surface on the side of the plaster intended to be directed outwards from the person in use. On the skin adhesive surface a covering sheet/foil may be applied, which is removed just before application of the tracheostoma device holder. The covering sheet facilitates transportation, and maintains skin adhesive ability of the skin adhesive surface. A plaster of this kind is disclosed in EP 0 078 685 A1.

It is however a problem associated with the application of the tracheostoma device holder after the removal of the covering sheet, since the throat of the person receiving the tracheostoma device holder by no means is planar. It is difficult to adhere the tracheostoma device holder in the pit in between the stemocleidomastoid muscles, at persons with sunken stomas, i.e. stomas that has sunken into the throat of the person, since the adhesive surface of the tracheostoma device holder inevitably will adhere to the walls of the pit before reaching the bottom of the pit with the central portion of the system. Sunken stomas are very frequent in the group of persons not having the two vertical stemocleidomastoid muscles on the neck cut during laryngectomy. As a result, it is very common that the tracheostoma device holder flip over, since the bad connection between adhesives and skin and the axial displacement of the speech pressure resulting in loosening of the tracheostoma device holder and need of unduly high speech pressure. Still further, the skin beneath the tracheostoma device holder will exude sweat, which will hamper the sealing between the skin and the tracheostoma device holder. Traditional wound dressings lose their ability to stick to skin in the presence of water—a major component of sweat—shortening their lifespan.

Furthermore, in many hospitals the surgical steps during laryngectomy are adapted for creating stomas of substantially planar natures, to comply with the tracheostoma device holder system presently on the market. This adaptation includes the cutting of the two vertical stemocleidomastoid muscles on the neck.

Hence, an improved tracheostoma device holder would be advantageous, and in particular a tracheostoma device holder allowing for convenient application of the tracheostoma device holder with improved positioning ability, while simultaneously decreasing the risk of loosening of skin adhesion close to the tracheostoma, due to for example sweat exuding, also in persons with sunken tracheostomas, thus keeping speech pressure at a convenient level.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a tracheostoma device holder for holding a tracheostoma device superimposed of a tracheostoma of a person, said tracheostoma device holder comprising: a flexible skirt for attachment over a tracheostoma via a skin adhesive proximal side thereof, said skirt being provided with a through hole; a tubular tracheostoma device fitting, arranged circumferentially of the through hole, said tubular tracheostoma device fitting extending distally from the distal side of the skirt; wherein the skirt having at least two sheets, in form of a distal end sheet comprising a skin adhesive hydrogel or hydrocolloid, and a support sheet proximally of said distal end sheet, said support sheet comprising polyurethane.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 4b is a cross-sectional view of the section A-A from FIG. 4a.

DESCRIPTION OF EMBODIMENTS

The following description focuses on an embodiment of the present invention applicable to a tracheostoma device holder, for holding a tracheostoma aid device over the stoma of a person. A tracheostoma aid device may in this context be a tracheostoma valve, HME, speech valve, etc., or combinations thereof.

Figure 1:
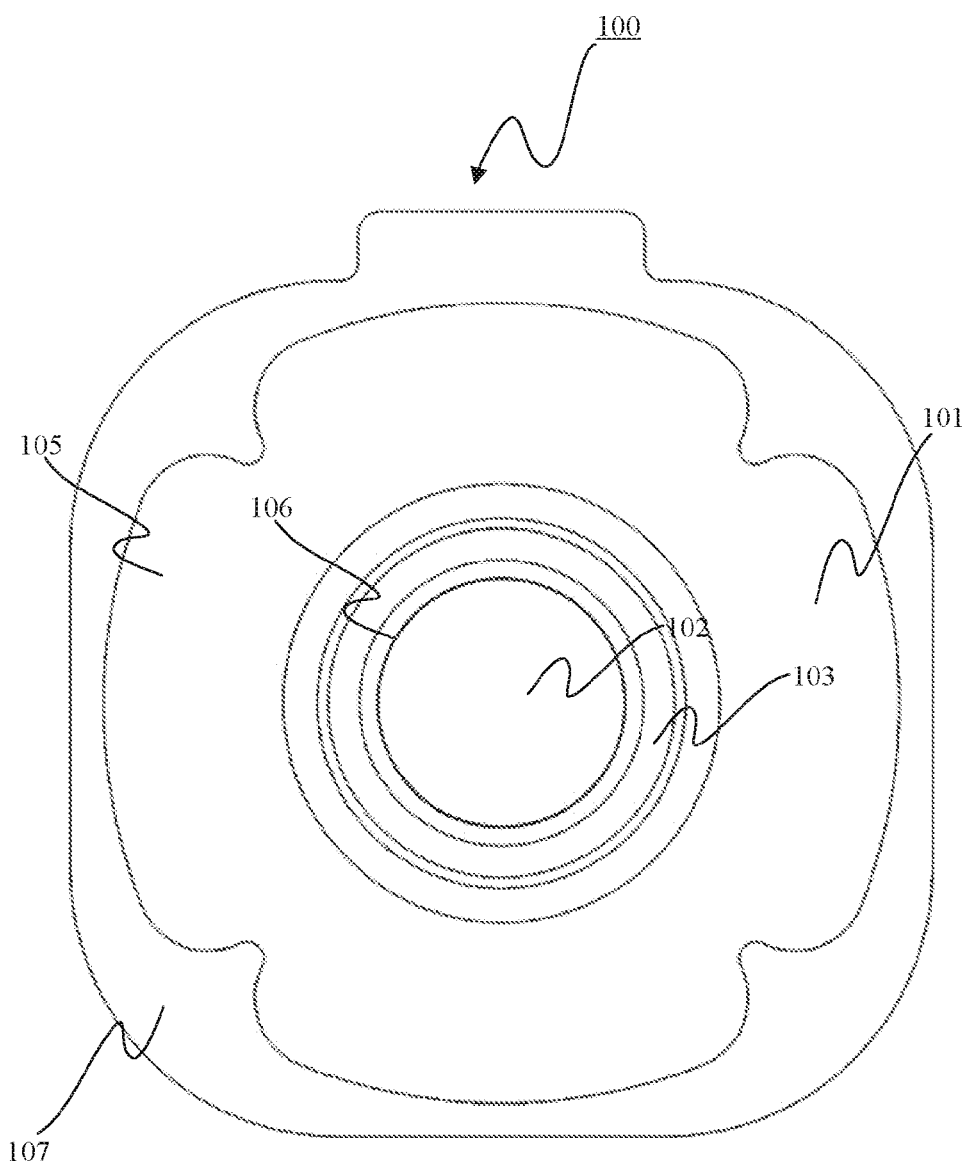
FIG. 1 is a perspective front-view of a tracheostoma device holder according to an embodiment of the invention.
Figure 2:
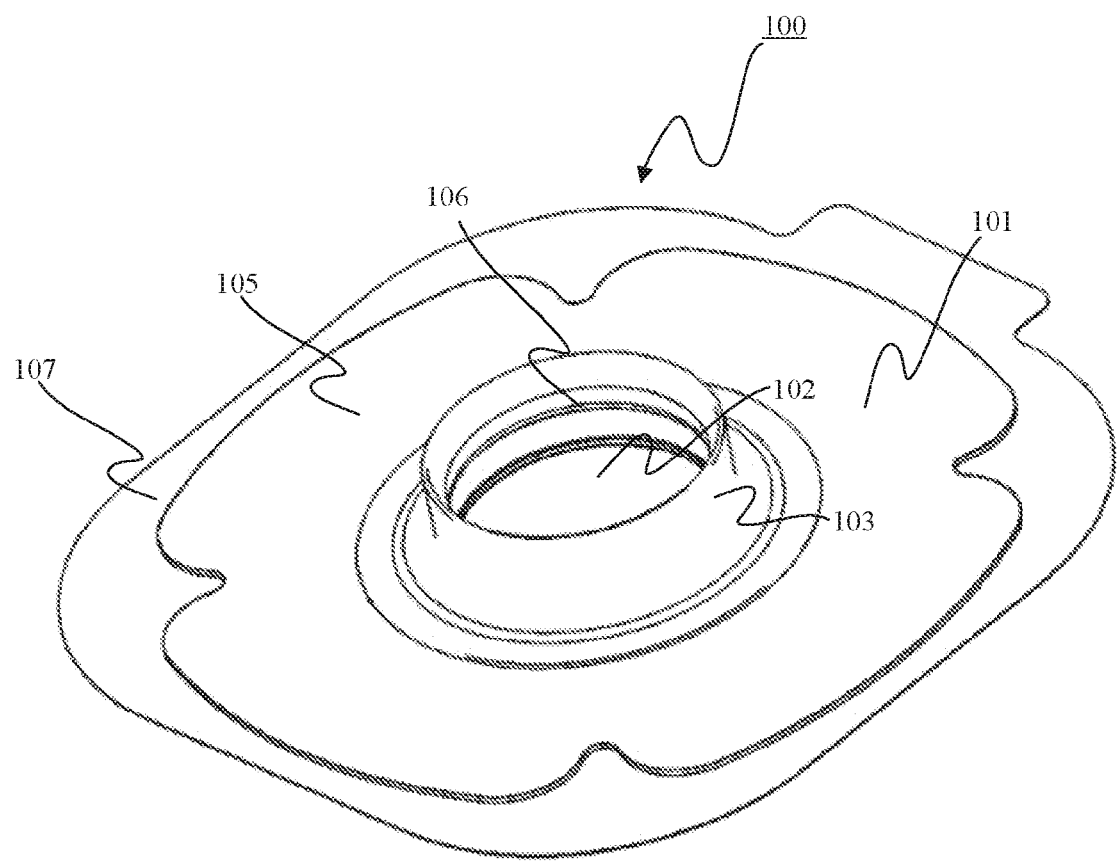
FIG. 2 is an isometric view of a tracheostoma device holder according to an embodiment of the invention.
Figure 3:
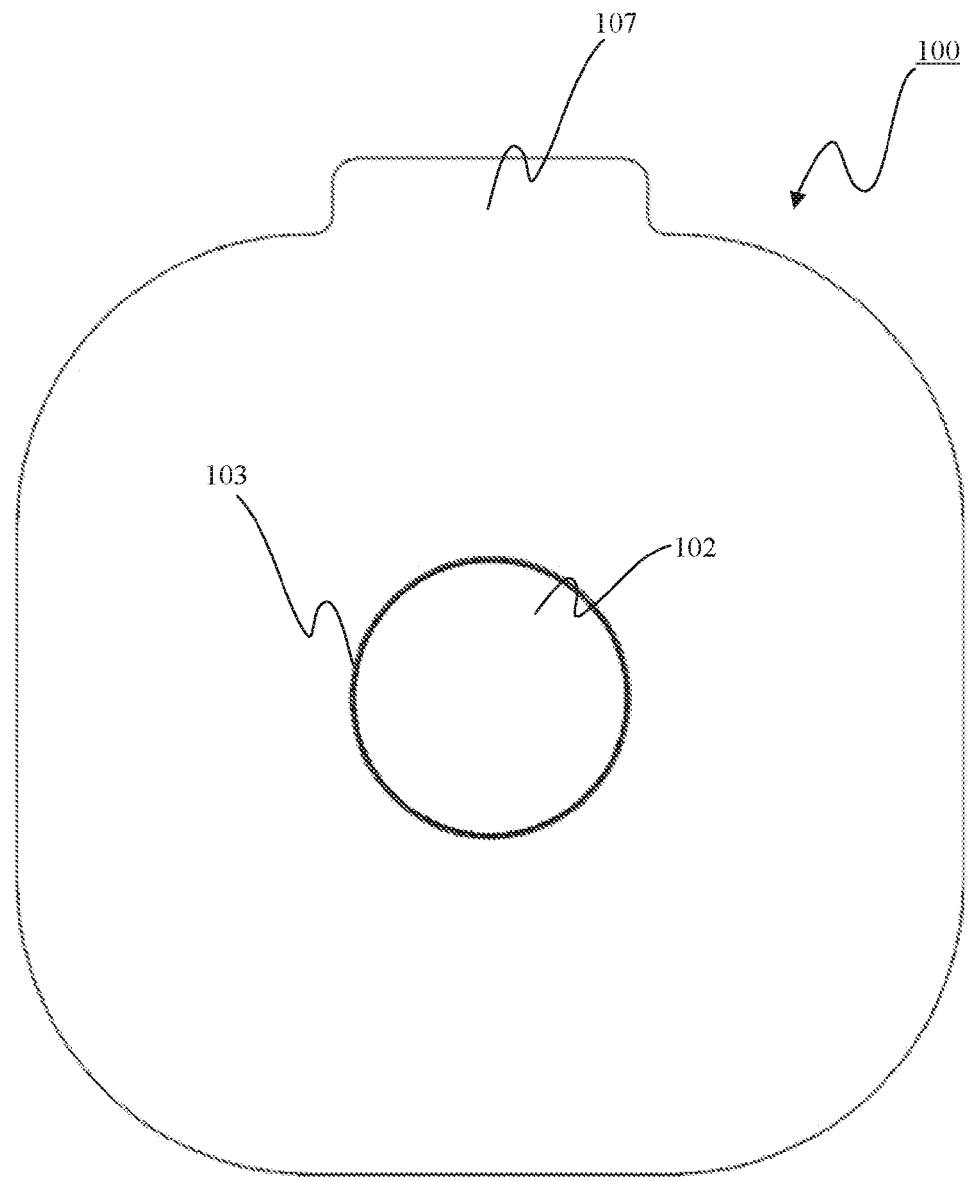
FIG. 3 is a perspective rear-view of a tracheostoma device holder according to an embodiment of the invention.
Figure 4A:
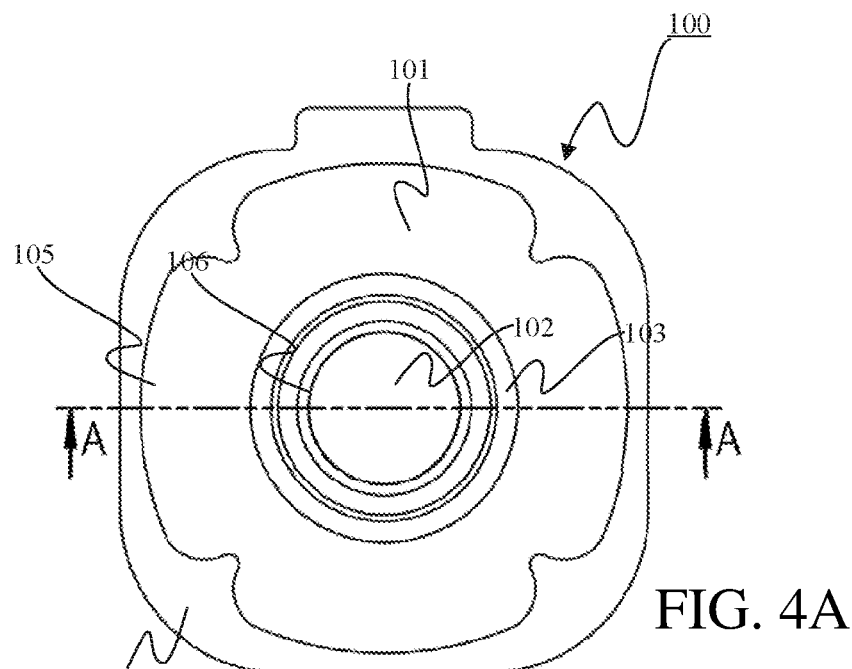
FIG. 4a is a perspective front-view of a tracheostoma device holder similar to FIG. 1, comprising a cross-section indicator A-A.
Figure 4B:
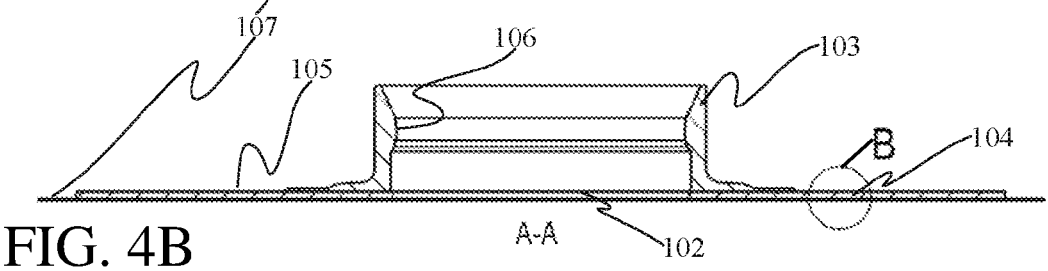
Figure 4C:
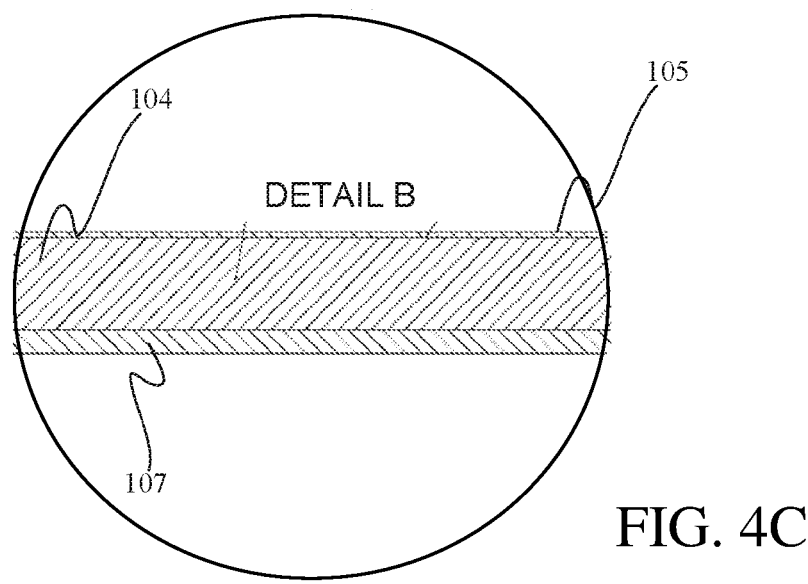
FIG. 4c is a detailed view of the area B of FIG. 4b showing layers of the tracheostoma device holder.

In FIGS. 1 to 4 a tracheostoma device holder 100 for holding a tracheostoma device superimposed of a tracheostoma of a person is disclosed. The tracheostoma device holder 100 comprises a flexible skirt 101 for attachment over a tracheostoma via a skin adhesive proximal side thereof. The skirt 101 is provided with a through hole 102. The tracheostoma device holder 100 also comprises a tubular tracheostoma device fitting 103. The tubular tracheostoma device fitting 103 is arranged circumferentially of the through hole 102. The tubular tracheostoma device fitting 103 extends distally from the distal side of the skirt 101. The skirt 101 comprises a distal end sheet 104 (FIG. 4.b-c). The distal end sheet comprises, such as being consisting of, a skin adhesive hydrogel or hydrocolloid. When the distal end sheet 104 comprises a skin adhesive hydrogel or hydrocolloid the skin underneath the skirt may be allowed to exude sweat without significant loss of skin adherence between skin and tracheostoma device holder 100. Hydrogels contain a large quantity of water already, which allows them to tolerate the additional water from sweat. Also, the compressibility, flexibility and formability allows for the distal end sheet 104 to take up discrepancies in skin structure and allow for easy stoma access.

The skin adhesive hydrogel may for this purpose be a hydrogel comprising polyacrylamide and poly(acrylamide-hydroxyethyl methacrylate). A hydrogel made from polyacrylamide and poly(acrylamide-hydroxyethyl methacrylate) has especially good mechanical strength and adhesion, for the intended purpose. The copolymer from acrylamide and hydroxyethyl methacrylate is inert to cells, making it suitable for skin contact materials.

Another suitable hydrogel for this purpose is a hydrogel comprising a high molecular weight water-soluble polyvinylpyrrolidone having ring opened pyrrolidone groups providing at least $1.5 \times 10^{-2}$ milliequivalents of carboxylic acid groups per gram of polymer, and a water-soluble multifunctional amine-containing polymer selected from the group consisting of polyethyleneimine, amine-terminated polyethylene oxide, amine-terminated polyethylene/polypropylene oxide, polymers of dimethyl amino ethyl methacrylate and copolymers of dimethyl amino ethyl methacrylate and vinyl pyrrolidone. Yet another suitable hydrogel for this purpose is a hydrogel comprising at least one cationic acrylate selected from the group consisting of acrylates made from acrylic esters of quaternary chlorides and/or sulfates or acrylic amides of quaternary chlorides.

The distal end sheet 104 may comprise non-woven fibers. Suitable non-woven fibers comprise polypropylene, such as being polypropylene non-woven fibers.

The distal end sheet 104 may comprise polystyrene particles, such as polystyrene nanoparticles. This improves the mechanical properties and induces pressure sensitive adhesiveness. It has been found that there is a link between the rheological flow properties and the adhesive properties of hydrogels. Nanoparticles of polystyrene can keep the rheological behavior constant even if the gel absorbs a large amount of fluid, which is especially beneficial for in the field of tracheostoma device holders.

Proximally of—such as adjacent and attached to—the distal end sheet 104 a support sheet 105 is provided. The support sheet 105 is preferably of a material allowing for the skin underneath the tracheostoma device holder 100 to continue breathing, not only through the distal end sheet 104 but also through the support sheet 105. Additionally, it should be compatible with the distal end sheet 104 comprising hydrogel or hydrocolloid as well as maintaining the compressibility, flexibility and formability of the distal end sheet 104. For these purposes it has been found that the support sheet 105 preferably comprises, such as consists of, polyurethane.

The tracheostoma device fitting 103 is made of a flexible and resilient material. In one preferred alternative, the tracheostoma device fitting 103 comprises, such as is made of, polyurethane. When the tracheostoma device fitting 103 is made of polyurethane the tracheostoma device fitting 103 may be ultrasound welded to the support sheet 105. In another preferred alternative the tracheostoma device fitting 103 comprises, such as is made of, a thermoplastic elastomer based on styrene block copolymers (TPS), such as styrene ethylene butylene styrene (SEBS). Up to this point, tracheostoma device fittings have been made of other plastic or rubber materials, due to manufacturing reasons. However, the present inventors have found that it is possible to ultrasound weld the tracheostoma device fitting 103 of polyurethane and TPS, such as TPS-SEBS, onto the polyurethane support sheet 105, while maintaining sealing effect upon use, i.e. patient exhalation and pressure differences from this. In such configuration, the skirt 101 will extend laterally as a flange from the tubular tracheostoma device fitting 103, in relation to a central axis of the through hole 102. Similarly, the tubular tracheostoma device fitting 103 extends axially and distally from the skirt 101, in accordance with above. The tracheostoma device fitting 103 comprises an annular recess 106 at its inside/lumen wall. This recess 106 allows for retaining cooperation with a corresponding and matching annular rib on a tracheostma device intended and adapted for cooperation with the tracheostoma device fitting 103. Alternatively, the inside/lumen wall of the tracheostoma device fitting 103 may be provided with a rib, to correspond in a retaining manner with an annular recess on the tracheostoma device holder, in the same way. The recess or rib 106 may extend continuously or discontinuously along the inside of a side wall of the tubular tracheostoma device fitting 103.

Since the skirt 101 and the tracheostoma device fitting 103 may be made of different materials, these parts may not be injection molded into a monolithic body. Instead, the skirt 101 may be overmolded to the tracheostoma device fitting 103, or vice versa. In fact, since sheet material, such that the combination of the distal end sheet 104 and the support sheet 105, most often and conveniently are manufactured through calendaring, it is not possible to incorporate the device fitting 103 in a simultaneous injection molding process. Instead, the device fitting 103 needs to be applied and fixed to the skirt 101 after the manufacturing thereof—alternatively also after punching the through hole 102 is provided. The process of fixing the device fitting 103 onto the skirt 101—while maintaining the function of the tracheostoma device holder 100—is therefore of importance, and so is the combination of materials and process selection.

The distal side of the tracheostoma device holder 100 can be provided with a release lining 107. The release lining 107 can be made of a polymer, for example, it can be formed of siliconised PET.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A tracheostoma device holder for holding a tracheostoma device superimposed on a tracheostoma of a person, said tracheostoma device holder comprising:
   a flexible skirt for attachment over the tracheostoma via a proximal side of a skin adhesive, said flexible skirt being provided with a through hole;
   a tubular tracheostoma device fitting arranged circumferentially around the through hole, said tubular tracheostoma device fitting extending distally from a distal side of the flexible skirt;
   wherein the flexible skirt has at least two sheets including a distal end sheet and a support sheet, said distal end sheet comprising a skin adhesive hydrogel or hydrocolloid, said support sheet being proximal to said distal end sheet, and said support sheet comprising polyurethane; and
   wherein said distal end sheet comprises non-woven fibers and said non-woven fibers comprise polypropylene.

2. The tracheostoma device holder according to claim 1, wherein said support sheet is arranged adjacent said to distal end sheet.

3. The tracheostoma device holder according to claim 2, wherein said distal end sheet comprises said hydrogel, said hydrogel comprising polyacrylamide and poly(acrylamide-hydroxyethyl methacrylate).

4. The tracheostoma device holder according to claim 1, wherein said distal end sheet comprises said hydrogel, said hydrogel comprising a high molecular weight water-soluble polyvinylpyrrolidone having ring opened pyrrolidone groups providing at least $1.5\times10^{-2}$ milliequivalents of carboxylic acid groups per gram of polymer, and a water-soluble multifunctional amine-containing polymer selected from the group consisting of polyethyleneimine, amine-terminated polyethylene oxide, amine-teminated polyethylene/polypropylene oxide, polymers of dimethyl amino ethyl methacrylate and copolymers of dimethyl amino ethyl methacrylate and vinyl pyrrolidone.

5. The tracheostoma device holder according to claim 1, wherein said distal end sheet comprises said hydrogel, said hydrogel comprising at least one cationic acrylate selected from the group consisting of acrylates made from acrylic esters of quaternary chlorides or sulfates or acrylic amides of quaternary chlorides.

6. The tracheostoma device holder according to claim 1, wherein said distal end sheet comprises polystyrene particles including polystyrene nanoparticles.

7. The tracheostoma device holder according to claim 1, wherein the tubular tracheostoma device fitting is provided with an annular continuous or discontinuous recess or rib on a side wall thereof.

8. The tracheostoma device holder according to claim 7, wherein the annular continuous or discontinuous recess or rib is arranged on an inside of the side wall.

9. The tracheostoma device holder according to claim 1, wherein the tubular tracheostoma device fitting comprises polyurethane.

10. The tracheostoma device holder according to claim 1, wherein the tubular tracheostoma device fitting comprises a thermoplastic elastomer based on styrene block copolymers.

11. The tracheostoma device holder according to claim 10, wherein the thermoplastic elastomer based on styrene block copolymers is styrene ethylene butylene styrene.

12. A method of manufacturing a tracheostoma device holder, comprising:
   providing a flexible skirt including a through hole, and a tubular tracheostoma device;
   shaping the flexible skirt from a sheet material, such that the flexible skirt is provided with at least two sheets including a distal end sheet and a support sheet, said distal end sheet comprising a skin adhesive hydrogel or hydrocolloid, said support sheet being proximal to said distal end sheet, and said support sheet comprising polyurethane, wherein said distal end sheet comprises non-woven fibers and said non-woven fibers comprise polypropylene;
   arranging the through hole in the flexible skirt; and
   ultrasound welding the tracheostoma device fitting circumferentially of the through hole, such that said tubular tracheostoma device fitting extending distally from a distal side of the flexible skirt.

13. The method according to claim 12, wherein the tracheostoma device fitting comprises polyurethane.

14. The method according to claim 12, wherein the tracheostoma device fitting comprises a thermoplastic elastomer based on styrene block copolymers.

15. The method according to claim 14, wherein the thermoplastic elastomer based on styrene block copolymers is styrene ethylene butylene styrene.

16. A tracheostoma device holder for holding a tracheostoma device on a tracheostoma of a person, comprising:
- a flexible skirt for attachment over the tracheostoma via a proximal side of a skin adhesive, said flexible skirt being provided with a through hole;
- a tubular tracheostoma device fitting arranged circumferentially of the through hole, said tubular tracheostoma device fitting extending distally from a distal side of the flexible skirt;
- wherein the flexible skirt has at least two sheets including a distal end sheet and a support sheet, said distal end sheet comprising a skin adhesive hydrogel or hydrocolloid, said support sheet being proximal to said distal end sheet, and said support sheet comprising polyurethane; and
- wherein said distal end sheet comprises non-woven fibers and said non-woven fibers are formed from polypropylene.

17. The tracheostoma device holder according to claim 16, wherein said support sheet is arranged adjacent to said distal end sheet.

\* \* \* \* \*